United States Patent
Tsukamoto et al.

(10) Patent No.: US 9,653,249 B2
(45) Date of Patent: May 16, 2017

(54) TRANSMISSION TYPE TARGET, RADIATION GENERATING TUBE HAVING THE TRANSMISSION TYPE TARGET, RADIATION GENERATOR HAVING THE RADIATION GENERATING TUBE, AND RADIATION IMAGING APPARATUS HAVING THE RADIATION GENERATOR

(71) Applicant: CANON KABUSHIKI KAISHA, Tokyo (JP)

(72) Inventors: Takeo Tsukamoto, Kawasaki (JP); Takao Ogura, Yokohama (JP); Shuji Yamada, Atsugi (JP); Yoichi Ikarashi, Fujisawa (JP); Nobuhiro Ito, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 58 days.

(21) Appl. No.: 14/440,856

(22) PCT Filed: Oct. 24, 2013

(86) PCT No.: PCT/JP2013/006287
§ 371 (c)(1),
(2) Date: May 5, 2015

(87) PCT Pub. No.: WO2014/076886
PCT Pub. Date: May 22, 2014

(65) Prior Publication Data
US 2015/0311026 A1  Oct. 29, 2015

(30) Foreign Application Priority Data

Nov. 15, 2012  (JP) .................................. 2012-251083

(51) Int. Cl.
*H01J 35/02* (2006.01)
*H01J 35/32* (2006.01)
(Continued)

(52) U.S. Cl.
CPC .............. *H01J 35/08* (2013.01); *C23C 16/06* (2013.01); *G01N 23/04* (2013.01); *H01J 35/32* (2013.01);
(Continued)

(58) Field of Classification Search
CPC ............. H01J 35/02; H01J 35/32; H05G 1/06
(Continued)

(56) References Cited

U.S. PATENT DOCUMENTS 4,972,449 A * 11/1990 Upadhya ............... H01J 35/108
378/143
5,148,462 A    9/1992 Spitsyn
(Continued)

FOREIGN PATENT DOCUMENTS

CN  2242521 Y  12/1996
CN  101582365 A  11/2009
(Continued)

OTHER PUBLICATIONS

"Carbon self-diffusion in tungsten carbide", Buhsmer, C.P. and Crayton, P.H., J. Mater. Sci., 1971, vol. 6, pp. 981-988.

*Primary Examiner* — David A Vanore
(74) *Attorney, Agent, or Firm* — Canon U.S.A. Inc., IP Division

(57) ABSTRACT

The present invention relates to a transmission type target having a diamond base material as the transmissive base material. The transmission type target includes a target layer containing a metal carbide constituted of at least one metal selected from the group consisting of molybdenum, tantalum, and tungsten and carbon; and a diamond base material supporting the target layer. The transmission type target inhibits the composition of the target layer from varying (Continued)

with the drive history of the transmission type target and inhibits the output of radiation from varying over a long time.

32 Claims, 9 Drawing Sheets

(51) Int. Cl.
    *H01J 35/08*     (2006.01)
    *C23C 16/06*     (2006.01)
    *G01N 23/04*     (2006.01)

(52) U.S. Cl.
    CPC ... *H01J 2235/081* (2013.01); *H01J 2235/087* (2013.01)

(58) Field of Classification Search
    USPC .................................................. 378/121, 143
    See application file for complete search history.

(56) References Cited

U.S. PATENT DOCUMENTS

| | | | |
|---|---|---|---|
| 7,359,487 B1 | 4/2008 | Newcome | |
| 9,230,774 B2* | 1/2016 | Yanagisawa | H01J 35/18 |
| 9,251,995 B2* | 2/2016 | Ogura | G01N 23/04 |
| 9,257,254 B2* | 2/2016 | Ogura | H01J 35/08 |
| 9,281,158 B2* | 3/2016 | Ogura | H01J 35/18 |
| 9,390,881 B2* | 7/2016 | Yun | G21K 1/06 |
| 9,408,577 B2* | 8/2016 | Tamura | A61B 6/025 |
| 2003/0185344 A1* | 10/2003 | Ukita | H01J 35/08 378/143 |
| 2008/0075229 A1 | 3/2008 | Ryan | |
| 2013/0129045 A1* | 5/2013 | Ogura | H01J 5/18 378/62 |
| 2014/0126701 A1* | 5/2014 | Ogura | H01J 35/08 378/121 |
| 2014/0153695 A1* | 6/2014 | Yanagisawa | G01N 23/04 378/62 |
| 2014/0205071 A1* | 7/2014 | Ikarashi | H01J 35/08 378/111 |
| 2014/0211919 A1* | 7/2014 | Ogura | H01J 35/08 378/62 |
| 2015/0311026 A1* | 10/2015 | Tsukamoto | H01J 35/08 378/62 |
| 2016/0155598 A1* | 6/2016 | Shiozawa | H01J 35/16 378/62 |

FOREIGN PATENT DOCUMENTS

| | | |
|---|---|---|
| CN | 102013378 A | 4/2011 |
| CN | 102257591 A | 11/2011 |
| EP | 2293318 A1 | 3/2011 |
| JP | 2002-527856 A | 8/2002 |
| JP | 2003-505845 A | 2/2003 |
| JP | 2003-526179 A | 9/2003 |
| JP | 2007-305565 A | 11/2007 |
| JP | 2009-545840 A | 12/2009 |
| JP | 2012-138168 A | 7/2012 |
| WO | 00/70645 A1 | 11/2000 |
| WO | 2012/140860 A1 | 10/2012 |

* cited by examiner

TRANSMISSION TYPE TARGET, RADIATION GENERATING TUBE HAVING THE TRANSMISSION TYPE TARGET, RADIATION GENERATOR HAVING THE RADIATION GENERATING TUBE, AND RADIATION IMAGING APPARATUS HAVING THE RADIATION GENERATOR

TECHNICAL FIELD

The present invention relates to a radiation generator that emits X-rays having a wavelength in the range of 1 pm to 10 nm and is applicable to medical instruments, nondestructive inspection systems, and other apparatuses. In particular, the invention relates to a transmission type target including a target layer and a diamond base material supporting the target layer. The invention further relates to a radiation generating tube having the transmission type target, a radiation generator having the radiation generating tube, and a radiation imaging apparatus having the radiation generator.

BACKGROUND ART

The need for compact and light portable medical modalities has been increased by changes in social situations, such as provision of home care systems and expansion in the range of emergency care. Recently, in order to respond to such a need, various medical modalities have been developed with the progress in analytical and diagnostic technologies in the medical field. Radiation imaging apparatuses having radiation generators are large in size and are therefore mainly installed in hospitals, medical examination institutions, and other facilities. The installed medical modalities have been utilized by regularly setting an operation period and an idle period including the time for maintenance.

Such a radiation imaging apparatus having a radiation generator is also required to be modified into a medical modality applicable to home care or emergency care for disasters and accidents by increasing the operating ratio of the apparatus through enhancement of durability and reduction of maintenance requirement.

One main factor that determines the durability of a radiation generator is the durability of the target serving as a source of generating radiation such as X-rays. The target generally has a laminated structure, and it is known that the maintenance of "adhesion" between the layers of the target for a long time is important for enhancing the durability of the target.

In a radiation generator that generates radiation by irradiation of a target with electron beams, the "radiation generation efficiency" of the target is less than 1%, and the majority of the energy injected into the target is converted into heat. If the "dissipation" of heat generated in a target to the outside of the target is insufficient, denaturation of the materials constituting the target and problems in "adhesion", such as peeling of a film due to the stress occurring in a layered structure, may occur.

It is known that "radiation generation efficiency" can be increased by using a transmission type target constituted of a thin-film form target layer that contains a heavy metal and a base material that transmits radiation and supports the target layer. PCT Japanese Translation Patent Publication No. 2009-545840 discloses a transmission type target of a rotating anode type having a "radiation generation efficiency" increased to 1.5 times that of a known reflection type target of a rotating anode type.

It is known that the use of diamond as the base material supporting the target layer of a transmission type target can accelerate "heat dissipation" from the target to the outside of the target. PCT Japanese Translation Patent Publication No. 2003-505845 discloses that the use of diamond as the base material supporting a tungsten target layer enhances heat dissipation and realizes microfocus. Diamond has high heat resistance and high thermal conductivity and also has high radiation transmissivity. Accordingly, diamond is a suitable material as a supporting base material of the transmission type target. The transmission type target of the present invention also employs a configuration in which diamond is used as a base material supporting the target layer.

SUMMARY OF INVENTION

Technical Problem

PCT Japanese Translation Patent Publication No. 2003-505845 discloses that the arrangement of an adhesion-enhancing layer of any material, which is not specifically disclosed in the document, between a target layer and a diamond base material enhances the adhesion between the target layer and the diamond base material. In radiation generators to which transmission type targets including adhesion-enhancing layers are applied, as disclosed in PCT Japanese Translation Patent Publication No. 2003-505845, however, radiation emission characteristics vary depending on the drive histories in some cases. The present inventors have diligently investigated and have revealed that a variation in the radiation output of a radiation generator is derived from a change in the composition of target layer of the transmission type target. More specifically, the present inventors have found that the carbon derived from a diamond base material supporting the target layer spreads into the target layer to cause a change in the composition of the target layer, resulting in a variation in radiation output.

Subsequently, the present inventors have analyzed the change in the composition of a target layer with a diffusion equation as a transportation problem of carbon. The analytical results will now be described.

First, a calculation model will be described. As the calculation model, a laminated target 90 composed of a diamond base material 51 and a target layer 52 of pure metal tungsten formed on the base material 51 is used. FIG. 8B schematically shows a cross section of the laminated target 90. FIG. 8C is an enlarged view of the range 54 in FIG. 8B, a portion from the interface 57 between the diamond base material 51 and the target layer 52 to the upper surface 58 of the target layer 52, showing the position 56 at which carbon derived from the diamond base material 51 has arrived and the diffusion length Ld(t) of the carbon. In the calculation, pulse drive of a target was performed at an average duty ratio of 1/1000 consisting of a 0.1-second exposure every 100 seconds at a temperature of 800 degrees Celsius and 1000 degrees Celsius, which are typical average operation temperatures of targets, by controlling the current density of incident electrons.

FIG. 8A shows the results, i.e., the dependency of the diffusion length Ld of carbon in the target layer 52 of the transmission type target 90 on the drive time. In the graph shown in FIG. 8A, the vertical axis indicates the diffusion length Ld of carbon diffused into the target layer 52 from the interface between the target layer 52 and the diamond base material 51. The first horizontal axis indicates the drive time (hour), and the second horizontal axis indicates the drive frequency (count).

The two plot lines in FIG. 8A correspond to temperature conditions of 800 degrees Celsius (broken line) and 1000 degrees Celsius (dotted line). In each plot line, the diffusion length is proportional to the 0.5 power of the drive time t. This indicates that carbon diffuses from the interface 57 toward the upper surface 58 of the target layer 52 with the drive time.

In estimation of the diffusion length Ld of carbon, the diffusion coefficient D0 ($m^2$/sec) and the activation energy of the diffusion coefficient Qx (kJ/mol) described in "Carbon self-diffusion in tungsten carbide", Buhsmer, C. P. and Crayton, P. H., J. Mater. Sci., 1971, vol. 6, pp. 981-988 were used in the Arrhenius's rule of diffusion coefficient: $D(T)=D0 \times \exp(-Qx/RT)$ and the stationary solution of diffusion length: $Ld(t)=2 \times (D(T) \times t)^{.5}$, wherein T denotes the thermodynamic temperature (K), t denotes the drive time (sec), and R denotes the gas constant (kJ/K/mol).

"Carbon self-diffusion in tungsten carbide", Buhsmer, C. P. and Crayton, P. H., J. Mater. Sci., 1971, vol. 6, pp. 981-988 specifically describes the diffusion coefficient D0 ($m^2$/sec) and the activation energy of the diffusion coefficient Qx (kJ/mol), which have been determined based on measured data of the diffusion phenomenon of carbon in tungsten carbide. It is obvious from the algebraic description of D(T) and Ld(t) that the diffusion length Ld of carbon lies between the two plot lines shown in FIG. 8A within an operation temperature of 800 degrees Celsius or more and 1000 degrees Celsius or less.

Next, the thickness of the target layer of the laminated target will be described. The target layer of a reflection type target is usually within a range of 1 micrometer or more and 1 millimeter or less. The lower limit of the thickness of the target layer of a reflection type target is determined in light of the electron penetration depth Dp that is defined by the tube voltage and the layer density of the target layer. The upper limit of the thickness of the target layer of a reflection type target is determined in light of the heat transfer in the thickness direction and the surface direction.

The thickness of the transmission type target can be within a range of 1 micrometer or more and 15 micrometers or less. In general, the thickness of the transmission type target is selected from the range of 1 micrometer or more and 9 micrometers or less. Such a lower limit of the thickness of a transmission type target is determined for the same reason as in the reflection type target. The upper limit of the thickness of the transmission type target is determined in light of the rate of attenuation of radiation in the thickness direction of the target layer, in addition to the heat transfer, and is restricted within a range lower than the thickness of the target layer of the reflection type target.

The graph shown in FIG. 8A demonstrates that the exposure drive for 104 times in total at an operation temperature of 800 to 1000 degrees Celsius results in a diffusion length Ld of carbon of 7.9 to 10.8 micrometers.

In the reflection type target, for example, in a reflection type target including a target layer 52 having a thickness of 100 micrometers, as shown in FIG. 8D, it is possible to secure a distance Lr of 89.2 to 92.1 micrometers from the electron incident surface 58 side, as a range to which carbon does not reach, on the radiation emission surface side (i.e., on the electron incident surface 58 side) of the target 52. This distance Lr of 89.2 to 92.1 micrometers is sufficiently large compared to the electron penetration depth Dp of 6 to 7 micrometers of the incident electrons of 100 keV against tungsten. It is obvious that the "radiation emission depth" in the target layer 52 contributing to generation of radiation is further restricted compared to the "electron penetration depth Dp". Accordingly, in the reflection type target, a "radiation emission depth" that is not affected by the diffusion of carbon can be secured in the target layer 52.

In the transmission type target, however, even in a transmission type target having a target layer 52 having a thickness of 8 micrometers, as shown in FIG. 8E, carbon reaches the range of the "electron penetration depth Dp" from the electron incident surface 58 side. More specifically, when the thickness of the target layer 52 is less than 14 micrometers, carbon reaches the range of the "electron penetration depth Dp" from the electron incident surface 58 side. This indicates that the composition of the target layer 52 varies with driving of the radiation generator.

Furthermore, since the transmission type target utilizes the radiation emitted from the supporting base material 51 side of the target layer 52, the region showing a high probability of penetration of the usable radiation to the front (i.e., to the direction of the surface on the side opposite to the surface supporting the target layer 52) corresponds to the deep side of the electron penetration depth Dp. Also in this point, the transmission type target is highly affected by diffusion of carbon during the radiation emission operation, compared to the reflection type target.

As described above, there is a problem "inherent to transmission type targets", i.e., the diffusion of carbon derived from diamond as a supporting base material and the radiation attenuation rate of the target layer itself are contradictory to each other in determination of the thickness of the target layer.

The laminated structure of which carbon supplying source is a diamond base material has been described as a calculation model. The same problem occurs in a structure having a metal carbide between the diamond base material and the target layer.

Accordingly, the present invention provides a transmission type target having a diamond base material as the transmissive base material, wherein the transmission type target has high reliability by inhibiting the composition from varying with the drive history of the target layer while maintaining the merits of satisfactory "radiation generation efficiency" and "heat dissipation". Furthermore, the present invention provides a radiation generator and a radiation imaging apparatus, having high reliability by inhibiting the radiation output from varying with the drive time history.

Solution to Problem

The transmission type target of the present invention includes a target layer containing a metal carbide constituted of at least one metal selected from the group consisting of molybdenum, tantalum, and tungsten and carbon and includes a carbon-containing base material supporting the target layer.

Advantageous Effects of Invention

In the transmission type target of the present invention, the carbon derived from the diamond base material is prevented from diffusing to the target layer even in the case of an operation history including high temperature by inhibiting the composition of the target layer from varying. As a result, the output or the quality of the radiation emitted from the target layer can be inhibited from varying. Furthermore, a radiation generating tube having the transmission type target of the present invention, a radiation generator having the radiation generating tube, and a radiation imaging apparatus having the radiation generator can each have enhanced reliability in durability.

Further features of the present invention will become apparent from the following description of exemplary embodiments with reference to the attached drawings.

BRIEF DESCRIPTION OF DRAWINGS

FIG. 4A-2 shows the example of a method of producing a transmission type target of the present invention.

FIG. 4B-1 shows an example of a method of producing a transmission type target of the present invention.

FIG. 4B-2 shows the example of a method of producing a transmission type target of the present invention.

FIG. 4B-3 shows the example of a method of producing a transmission type target of the present invention.

FIG. 4B-4 shows the example of a method of producing a transmission type target of the present invention.

FIG. 4C-1 shows an example of a method of producing a transmission type target of the present invention.

FIG. 4C-2 shows the example of a method of producing a transmission type target of the present invention.

FIG. 4C-3 shows the example of a method of producing a transmission type target of the present invention.

FIG. 4C-4 shows the example of a method of producing a transmission type target of the present invention.

DESCRIPTION OF EMBODIMENTS

Figure 1A:
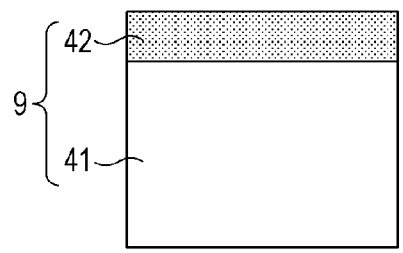
FIG. 1A is a schematic cross-sectional view showing a basic configuration example of the transmission type target of the present invention.

Embodiments of the target structure of the present invention and a radiation generator and a radiation imaging apparatus each having the target structure will now be exemplarily described in detail with reference to the drawings. Note that the materials, sizes, shapes, relative configurations, and other factors of the structures described in the following embodiments are not intended to limit the scope of the present invention unless specifically mentioned.

First, a basic configuration example of a radiation generating tube to which the transmission type target of the present invention can be applied will be described with reference to FIG. 2.

In this embodiment, the radiation generating tube 1 includes a transmission type target 9 having a target layer 42 and a diamond base material 41, an electron emission source 3 having an electron-emitting unit 2 facing the target layer 42 with a distance therebetween, and an envelope 6 having an interior space 13 in which the pressure is reduced. The electron-emitting unit 2 and the target layer 42 are contained in the interior space 13 or are arranged on the inner surfaces of the envelope 6 so as to face each other with the interior space 13 therebetween.

The electron emission source 3 is electrically connected to a drive circuit (not shown) disposed outside the envelope 6. The electron emission source 3 can have a current inlet terminal 4 for electrical connection to the drive circuit.

The electron emission source 3 is also connected to a cathode member (not shown) of an electrically conductive material. The structure composed of the electron emission source 3 and the cathode member is the cathode of the radiation generating tube 1 in this embodiment. The potential of the cathode is regulated to a cathodic potential. The cathode member may be disposed inside the envelope 6 or may be a structural member constituting a part of the envelope 6.

The electron-emitting unit 2 may be any electron emission element as long as the electron emission amount from the electron emission source 3 is electrically controlled by the drive circuit (not shown). Applicable examples of the electron-emitting unit 2 include cold cathode electron emission elements such as Spindt-type, SCE-type, MIM-type, and CNT-type; and hot cathode electron emission elements such as filament-type and impregnation-type. The electron emission source 3 can also have a focused grid (not shown).

The transmission type target 9 is electrically connected to an anode potential regulator (not shown) disposed outside the envelope 6. In this embodiment, the structure composed of the transmission type target 9 and the anode member is the anode of the radiation generating tube 1.

The anode member may be disposed inside the envelope 6 or may be a structural member constituting a part of the envelope 6, as in the cathode member.

The envelope 6 constitutes the radiation generating tube 1 as a vacuum container of which interior space 13 is evacuated. The envelope 6 should be constituted of a member having anti-atmospheric pressure strength for maintaining the structure in spite of the differential pressure between the outside and the inside of the vacuum container and having airtight for maintaining a predetermined degree of vacuum.

The degree of vacuum of the interior space 13 can be appropriately selected depending on the type of the electron emission source 3 and can be within a range of $1 \times 10^{-4}$ to $1 \times 10^{-8}$ Pa from the viewpoint of a longer life span of the electron emission source 3. Furthermore, a getter (not shown) may be disposed inside the envelope 6 or in a space communicating with the interior space 13, depending on the type of the electron emission source 3 or the necessary degree of vacuum.

Since the envelope 6 has a function of regulating the distance between the electron-emitting unit 2 and the target layer 42, the electron emission source 3 and the transmission type target 9 may be each connected to the envelope 6. In this embodiment, the envelope 6 can have a tubular member having electric insulating property for insulating high voltage applied between the electron-emitting unit 2 and the target layer 42. Such a tubular member can be constituted of an insulating material such as an inorganic oxide, e.g., ceramic or glass, an inorganic nitride, or an inorganic boride.

The cathode member and the anode member are each constituted of an electrically conductive material for exhibiting the potential-regulating function and can each be a metal material. Furthermore, the cathode member and the anode member can each be a metal material from the viewpoint of heat resistance in light of the operation temperature of the radiation generating tube 1 or from the viewpoint of agreement in the coefficient of linear expansion with that of the insulating tubular member. For example, a metal material such as Kovar (U.S. trademark own by CRS HOLDINGS, INC., Ni—Co—Fe alloy), Monel (U.S. trademark co-owned by Special Metals Corporation and HUNTINGTON ALLOYS CORPORATION, Ni—Cu—Fe alloy), or stainless steel can be used.

Figure 2:
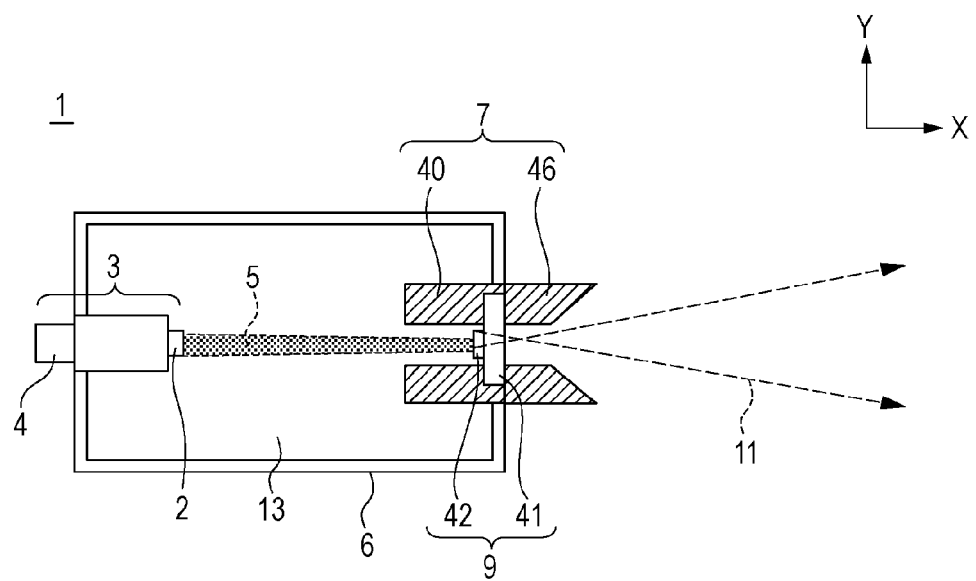
FIG. 2 is a schematic cross-sectional view showing a configuration example of a radiation generating tube having the transmission type target of the present invention.

As shown in FIG. 2, the radiation generating tube 1 further includes a shield 7 for restricting the emission direction of the radiation generated by the transmission type target 9. That is, a light-weight radiation generator can be provided by intensively arranging the shield 7 near the source of radiation. The shield 7 can be composed of a back shield 40 disposed on the electron emission source 3 side with respect to the transmission type target 9 and a front shield 46 located on the side opposite to the electron emission source 3 with respect to the transmission type target 9.

Next, a radiation generator having the transmission type target of the present invention will be described with reference to FIG. 3.

Figure 3:
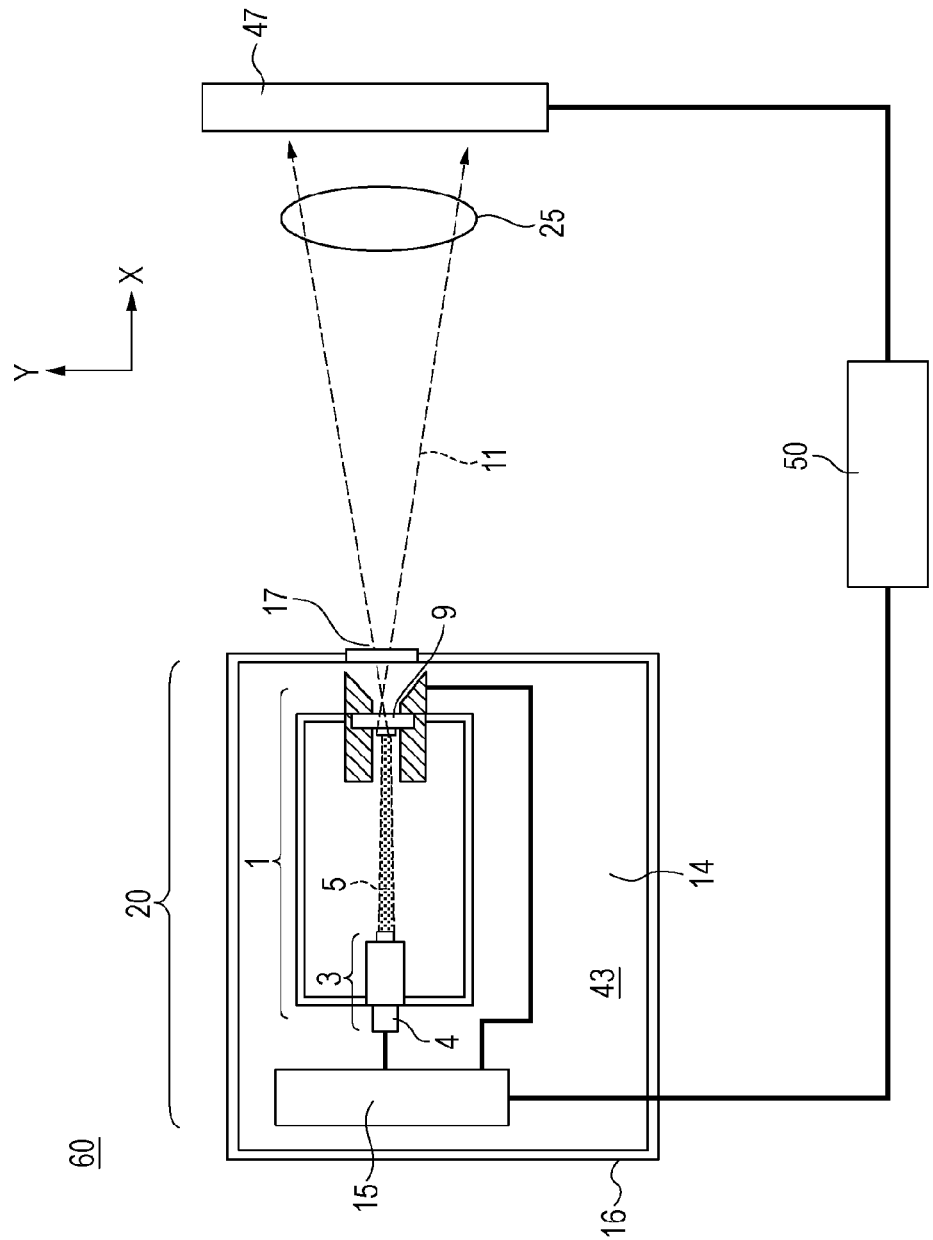
FIG. 3 is a configuration diagram of a radiation generator having the radiation generating tube of the present invention, and a radiation imaging apparatus.

As shown in FIG. 3, the radiation generator 20 includes a radiation generating tube 1 and a drive circuit 15 electrically connected to the radiation generating tube 1. In this embodiment, the drive circuit 15 includes an anode potential regulator and a cathode potential regulator that regulates the potentials of the anode and the cathode, respectively, of the radiation generating tube 1 and an electron gun-driving circuit that controls the amount of electron rays 5 emitted from the electron emission source 3. The radiation generator 20 may further include a container 16 having an interior space 43 for containing the radiation generating tube 1 and the drive circuit 15.

The container 16 can be in a form in which the interior space 43 is filled with an insulating liquid 14 (not shown) such as silicone oil or perfluoro oil. Such a form can enhance the heat dissipation and the pressure resistance of the radiation generator 20.

Furthermore, the radiation can be efficiently emitted to the outside of the radiation generator 20 by providing a transmission window 17 to the container 16 on the side facing the transmission type target 9.

As the anode potential regulator, a voltage source that can output a positive accelerating voltage Va of about several tens to two hundred to the cathode can be used.

The anode side output potential of the anode potential regulator can be selected depending on, for example, whether a subject is brought into contact with the anode member or the distance between the subject and the anode member. Specifically, the output potential can be ground potential (anode grounding), a half of the +Va value (middle point grounding), or +Va (cathode grounding).

Next, radiation imaging apparatus having the radiation generator of the present invention will be described with reference to FIG. 3.

As shown in FIG. 3, the radiation imaging apparatus 60 of the present invention includes a radiation detector 47 that detects the radiation emitted from the radiation generator 20 and permeated through a subject 25. In an embodiment, the radiation imaging apparatus 60 can further include a controlling unit 50 that controls the drive circuit 15 of the radiation generator 20 and receives radiological images from the radiation detector 47.

The controlling unit 50 can further have at least one function, such as a function of controlling the radiation detector 47, a function of displaying a radiological image for an operator, a function of receiving input manipulated by an operator, or a function of stopping the radiation generator according to an emergency stop order.

Next, a structure of the transmission type target, which is one of a feature of the present invention, will be described with reference to FIGS. 1A and 1B.

The transmission type target 9 includes a target layer 42 containing a target metal and a diamond base material 41 supporting the target layer 42.

The target layer 42 contains a carbide of at least one target metal selected from the group consisting of molybdenum (Mo), tantalum (Ta), and tungsten (W) in such a manner that the carbide is distributed in the thickness direction. A first feature is that "carbon is contained in the target layer 42 as a carbide", and the second feature is that the carbon constituting the metal carbide is "uniformly distributed in the thickness direction of the target layer 42".

The technical significance of the first feature, i.e., "the target layer 42 contains carbon as a carbide", will now be described in detail.

Diamond shows specific characteristics originated in the structure having strong sp3 bonds and high regularity. Among the specific characteristics of diamond, high heat resistance (melting point: 1600 degrees Celsius or more), high thermal conductivity (600 to 2000 W/m/K), and high radiation transmissivity (light element, atomic number: 6) are particularly excellent characteristics as a base material supporting the transmission type target. At the same time, diamond is low in wettability to molten metals and also is low in affinity with target metals, as obvious from the disagreement in coefficient of linear expansion with those of solid metals. Securement of high adhesion between the target layer 42 and the diamond base material 41 is required for improving the reliability of a transmission type target 9. The carbon contained in the target layer 42 is expected to bridge between the target layer 42 and the diamond base material 41 at the interface therebetween.

However, carbon allotropes and hydrocarbons as carbon compounds other than diamond are thermally unstable. Therefore, it is difficult that these carbon compounds continuously and stably function as an adhesive between the target layer 42 and the diamond base material 41 at the operation temperature of the transmission type target 9.

Molybdenum, tantalum, and tungsten contained in the target layer 42 of the present invention are metals exhibiting negative standard free energies of formation of carbides, and the metal carbides thereof are thermally stable. Molybdenum carbide, tantalum carbide, and tungsten carbide have high melting points ($Mo_2C$: 2692 degrees Celsius, TaC: 3880 degrees Celsius, and WC: 2870 degrees Celsius). The use of at least one of molybdenum carbide, tantalum carbide, and tungsten carbide as a material constituting the target layer 42 contributes to realization of a transmission type target 9 having high heat resistance.

Furthermore, in a target layer 42 containing carbon as a metal carbide, the metal carbide has a crystalline structure. This means that carbon atoms are distributed with a predetermined space density based on the grating density. The target layer 42 containing carbon at a predetermined space density can form a strong laminate interface resulting from the carbon-carbon interatomic bonds at the interface between the target layer 42 and the diamond base material 41.

Next, the technical significance of the second feature, i.e., "the target layer 42 contains carbon as a metal carbide uniformly in the thickness direction", will now be described in detail.

Due to the second feature, even if the transmission type target 9 is exposed to a high-temperature environment during the operation of the radiation generating tube 1, the "diffusion of carbon from the diamond base material 41 to the target layer 42" and the "diffusion of carbon in the target layer 42" are prevented to inhibit the composition of the target layer 42 from varying.

That is, due to the second feature, the target layer 42 contains carbon as a metal carbide uniformly in the thickness direction before the radiation output operation of the transmission type target 9. This exhibits a function of "reducing the gradient in concentration of carbon between" the diamond base material 41 and the target layer 42 and causes an effect of inhibiting the "diffusion of carbon from the diamond base material 41 to the target layer 42".

Furthermore, due to the second feature, the target layer 42 contains carbon as a metal carbide uniformly in the thickness direction before the radiation output operation of the transmission type target 9. This exhibits a function of "reducing the gradient in concentration of carbon in" the target layer 42 and causes an effect of inhibiting the "diffusion of carbon in the target layer 42".

As described above, in the target layer 42 having the first and the second features, the composition of the target layer 42 is stabilized. A radiation generating tube 1 having the transmission type target 42 can stabilize the output operation of the radiation generator 20 over a long time. This technical significance is very important in a transmission type target 9 that is difficult to have a sufficiently thick target layer 42 compared to the diffusion length Ld of carbon.

Note that the second feature of the present invention, i.e., the target layer 42 uniformly containing carbon in the thickness direction, means that carbon is contained in an arbitrary region in the thickness direction of the target layer 42 as a metal carbide.

Accordingly, the target layer 42 containing carbon uniformly in the thickness direction is not necessarily limited to a form having a constant carbon concentration in the thickness direction of the target layer. In another embodiment, the carbon concentration has a predetermined distribution within a range that exhibits an effect of inhibiting the composition of the target layer 42 from varying. Specifically, an embodiment in which the atomic concentration ratio of the maximum carbon concentration to the minimum carbon concentration is less than ten in the region of 90% of the target layer 42 in the thickness direction is encompassed in the present invention.

In addition, molybdenum, tantalum, and tungsten contained in the target layer 42 are all transition metals and can therefore each form a carbide crystalline structure having multiple carbon atoms, however, the stable crystalline structures of the carbides of these metals are those each having 1 or 0.5 carbon atom per a metal atom. In molybdenum, tantalum, and tungsten, hexagonal crystal dimolybdenum carbide, cubic crystal monotantalum carbide, and hexagonal crystal monotungsten carbide are the thermally most stable structures.

Accordingly, in the case of a target layer 42 containing molybdenum as the target metal, the structure of the target layer 42 can be inhibited from varying when the atomic concentrations of the metal carbides in the target layer 42 satisfy the relationship: dimolybdenum carbide ($Mo_2C$) concentration>monomolybdenum carbide (MoC) concentration. Accordingly, the heat resistance of a transmission type target is further enhanced by using a monolayer of dimolybdenum carbide ($Mo_2C$), which is the most stable structure, as the target layer 42.

Similarly, in the case of a target layer 42 containing tantalum as the target metal, the atomic concentrations of the metal carbides in the target layer 42 should satisfy the relationship: monotantalum carbide (TaC) concentration>ditantalum carbide ($Ta_2C$) concentration. Consequently, the heat resistance of a transmission type target is further enhanced by using a monolayer of monotantalum carbide (TaC), which is the most stable structure, as the target layer 42.

Similarly, in the case of a target layer 42 containing tungsten as the target metal, the atomic concentrations of the metal carbides in the target layer 42 should satisfy the relationship: monotungsten carbide (WC)>ditungsten carbide ($W_2C$). Consequently, the heat resistance of a transmission type target is further enhanced by using a monolayer of monotungsten carbide (WC), which is the most stable structure, as the target layer 42.

The present inventors have performed operation tests of transmission type targets having target layers of a stable hexagonal crystal dimolybdenum carbide, cubic crystal monotantalum carbide, or hexagonal crystal monotungsten carbide and have revealed that the hexagonal monotungsten carbide is the most stable. The reasons of this are not obvious, but it is believed that the hexagonal crystal monotungsten carbide has a higher thermal conductivity and a lower coefficient of linear expansion compared to those of other two carbides and thereby shows higher stability during operation than the others.

The target layer 42 can inhibit the electron damage of the diamond base material 41 while transmitting the radiation generated in the target layer 42 to the front when the thickness of the target layer 42 is about 1 to 1.5 times the electron penetration depth Dp, which is defined by the tube voltage Va of the radiation generating tube. The range of the electron penetration depth Dp is the heat-generating portion of the transmission type target 9. Accordingly, the metal carbide should be contained in the region from the surface of the target layer 42 to the electron penetration depth Dp from the viewpoints of high heat resistance and prevention of the variation in composition of the target layer 42.

In general, the electron penetration depth Dp is determined by the incident energy Ep (eV), i.e., the tube voltage Va (V) and the density of the target layer. In the present invention, the electron penetration depth Dp (m) is determined by the following Expression 1:

$$Dp = 6.67 \times 10^{-10} \times Va^{16}/rho \qquad \text{(Expression 1)},$$

the value of which well accords with the actual value in the range of $1 \times 10^4$ to $1 \times 10^6$ V of the incident energy Ep (=Va). In Expression 1, Va denotes a tube voltage (V), and rho denotes the density ($kg/m^3$) of the target layer. The density of the target layer may be determined by weighing and measurement of the thickness or may be determined by Rutherford backscattering spectrometry (RBS), which is suitable for measuring the density of a thin film.

Specifically, a target layer 42 having a thickness of 0.1 micrometers to several tens micrometers can inhibit delamination due to stress.

Figure 1B:
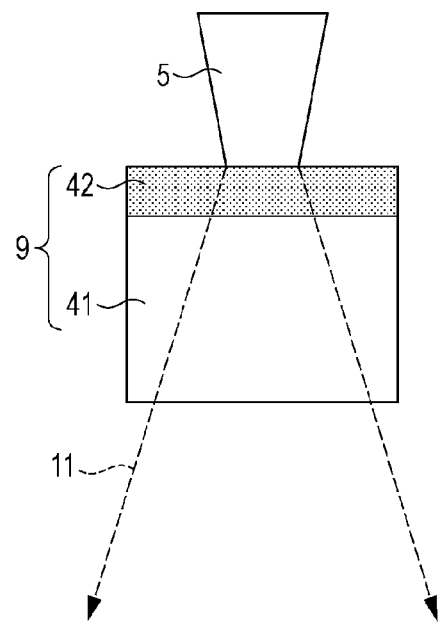
FIG. 1B is a schematic cross-sectional view showing an operation state of the basic configuration example of the transmission type target of the present invention.

Furthermore, though the target layer 42 can has a composition containing a target metal and another metal, the target layer 42 having a single composition composed of a carbide of a single target metal can sharpen the spectrum of the characteristic X-rays contained in the emitted radiation 11 shown in FIG. 1B. The metal carbide contained in the target layer 42 has a characteristic crystalline structure different from that of its pure metal form, i.e., molybdenum, tantalum, or tungsten, which can be observed by, for example, X-ray diffraction (XRD), high-resolution image with a transmission electron microscope (TEM), or electron diffraction (ED).

Next, the diamond base material of the transmission type target of the present invention will be described with reference to FIGS. 1A and 1B.

The diamond base material 41 can secure both thermal conductivity in the surface direction of the base material and radiation transmissivity by controlling the thickness of the diamond base material 41 to be 0.1 to 10 mm. The diamond base material 41 may be single-crystalline diamond or polycrystalline diamond, and single-crystalline diamond can provide higher thermal conductivity. Furthermore, the diamond base material 41 can enhance its shock resistance by containing nitrogen in a range of 2 to 800 ppm, which enables an improvement in flexibility of the radiation generator to which the transmission type target 9 of the present invention is applicable. In order to certainly support the target layer, however, polycrystalline diamond, which has a surface roughness larger than that of single-crystalline diamond, can secure an anchoring force against the diamond base material of the target layer.

In this embodiment, diamond base material 41 has been used. The base material supporting the target layer 42 applicable to the present invention can be selected from base materials containing carbon such as glassy carbon or diamond-like carbon containing sp3 bonds, in addition to the diamond base material 41.

Next, a method of forming the transmission type target 9 of the present invention will be described with reference to FIGS. 4A-1 to 4C-4.

Figures 1, 4A:
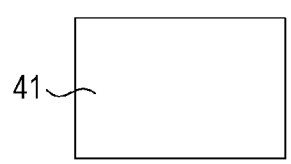
FIG. 4A-1 shows an example of a method of producing a transmission type target of the present invention.
Figures 2, 4A:
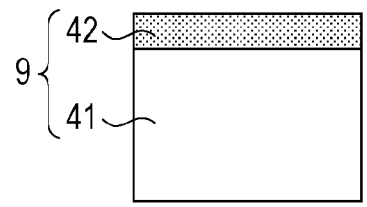
Figures 1, 4B:
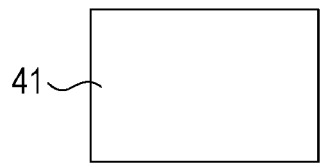
Figures 2, 4B:
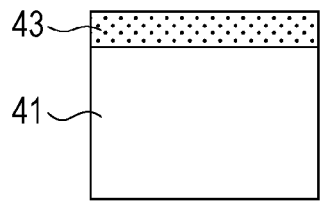
Figures 3, 4B:
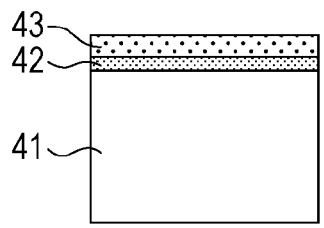
Figures 4, 4B:
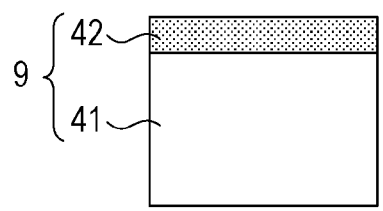

In a first method of forming a transmission type target 9, as shown in FIGS. 4A-1 and 4A-2, a metal carbide layer as the target layer 42 is formed on a diamond base material 41. The metal carbide layer can be formed by an arbitrary film-forming method such as chemical vapor deposition (CVD), physical vapor deposition, or thermal spraying. In a second method of forming a transmission type target 9, as shown in FIGS. 4B-1 to 4B-4, a laminate is formed by forming a metal layer 43 on a diamond base material 41, and the laminate is heated in a temperature range of 1000 degrees Celsius or more and 2000 degrees Celsius or less under a reduced-pressure atmosphere, a deoxidation atmosphere, or an inert gas atmosphere. In the method including metal layer formation and carbonization, carbon derived from the diamond base material 41 is dispersed in the metal layer 43, and the metal contained in the metal layer 43 can be carbonized. The time of the carbonization can be shortened by performing the heating within a temperature range of 1500 degrees Celsius or more and 2000 degrees Celsius or less.

Figures 1, 4C:
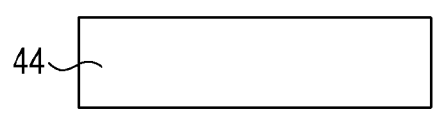
Figures 2, 4C:
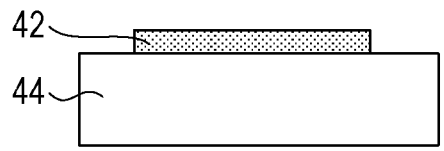
Figures 3, 4C:
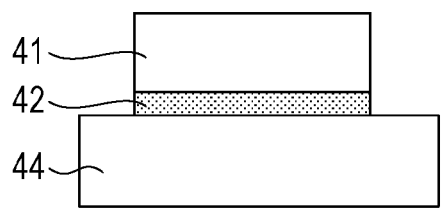
Figures 4, 4C:
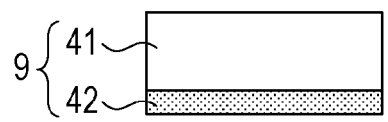

In addition, as shown in FIGS. 4C-1 to 4C-4, a transmission type target 9 can be formed by a method as a modification of the first and the second methods by forming a metal carbide layer 42 or a metal layer on a base material 44 constituted of a material having a low thermophysical temperature, then forming a diamond layer 41 by CVD or another process, and selectively removing the base material 44. As the thermophysical temperature of the base material 44, the melting point or the decomposition temperature is employed. When these temperatures of the base material 44 are lower than those of the target layer 42 or the diamond base material 41, the method of forming a transmission type target according to this embodiment can be carried out.

Next, modification examples of the transmission type target 9 of the present invention having a potential regulator for regulating the potential of the target layer 42 will be described with reference to FIGS. 5A to 5C.

A high voltage of about several tens to two hundred kilo-volts is applied between the target layer 42 and the electron-emitting unit 2 to stably regulate the potential of the target layer 42 from the viewpoint of withstand voltage. FIG. 5A shows an embodiment where a target layer 42 is formed on a diamond base material 41 in such a manner that the entire area of one surface of the diamond base material 41 is covered with the target layer 42 reaching the peripheral edge 61 of the base material 41. In this embodiment, the periphery 62 of the target layer 42 is electrically connected to an anode member (not shown) via a brazing material or a metallized layer (not shown).

Figure 5A:
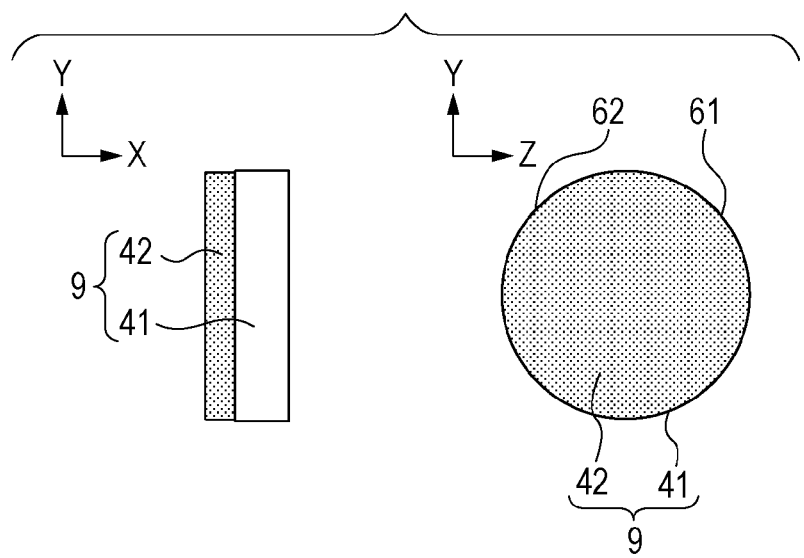
FIG. 5A shows a modification of the lamination of the transmission type target according to an embodiment of the present invention.
Figure 5B:
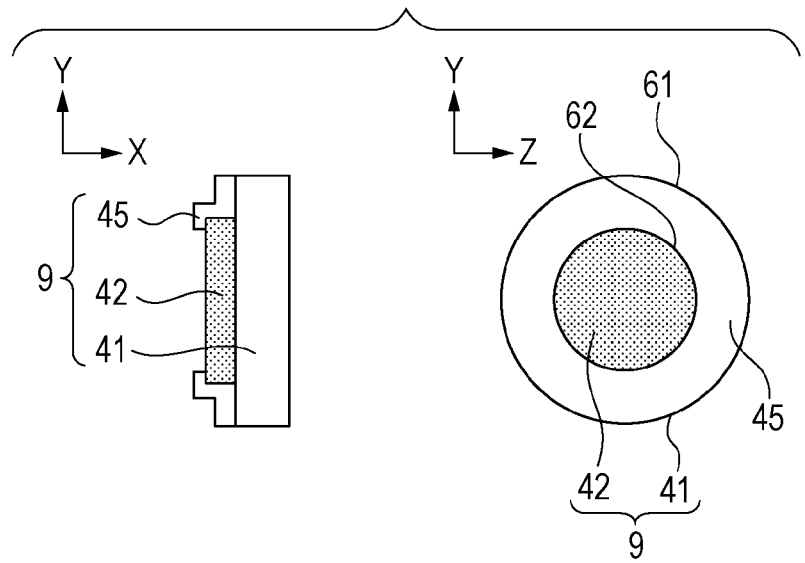
FIG. 5B shows a modification of the lamination of the transmission type target according to another embodiment of the present invention.

FIG. 5B shows an embodiment where a target layer 42 is formed on a diamond base material 41 in a partial area of one surface of the diamond base material 41 in such a manner that the circumference 62 of the target layer 42 is separated from the peripheral edge 61 of the diamond base material 41 with a predetermined distance. In this embodiment, target layer 42 is electrically connected to an anode member (not shown) via a circular electrode 45 in addition to a brazing material or a metallized layer.

Figure 5C:
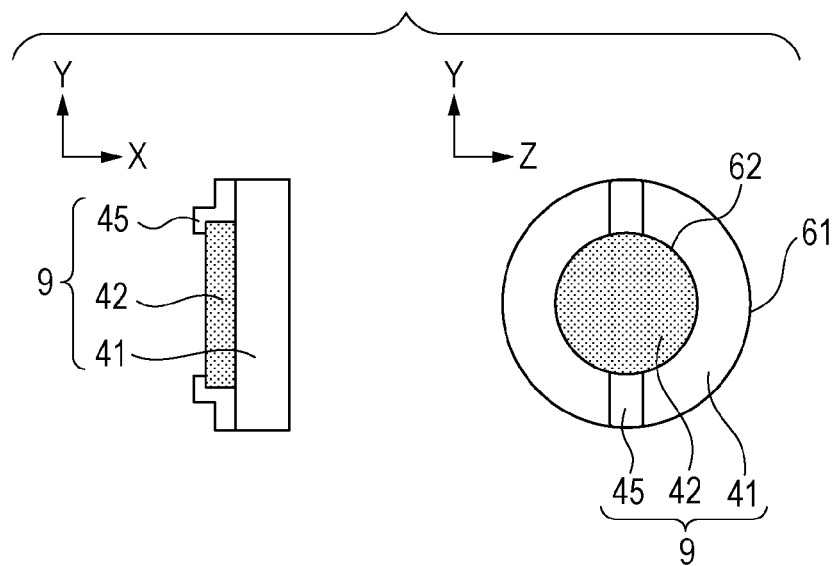
FIG. 5C shows a modification of the lamination of the transmission type target according to another embodiment of the present invention.

The electrode 45 may be formed on the entire surface of the diamond base material 41 as an underlying layer of the target layer 42 or may be formed so as to bridge between the target layer 42 and the peripheral edge 61 of the diamond base material 41 at a partial area of the circumference 62 of the target layer 42, as shown in FIG. 5C.

The electrode 45 may be constituted of a pure metal or may be a metal nitride, metal oxide, or metal carbide that has an electrical conductivity sufficient for regulating the potential of the target layer 42. When the electrode 45 is a metal carbide layer constituted of a carbide of a metal element different from the target metal contained in the target layer 42, the diffusion of carbon from the target layer 42 to the electrode 45 is inhibited, and the variation in the composition of the target layer 42 can be further inhibited.

Furthermore, the transmission type target of the present invention may have a metal carbide layer having a different composition from that of the target layer, as an intermediate layer, between the target layer and the diamond base material.

EXAMPLES

A radiation generator having the transmission type target of the present invention was produced by the procedure shown below, and the output stability during operation of the radiation generator was evaluated.

Example 1

Figure 6:
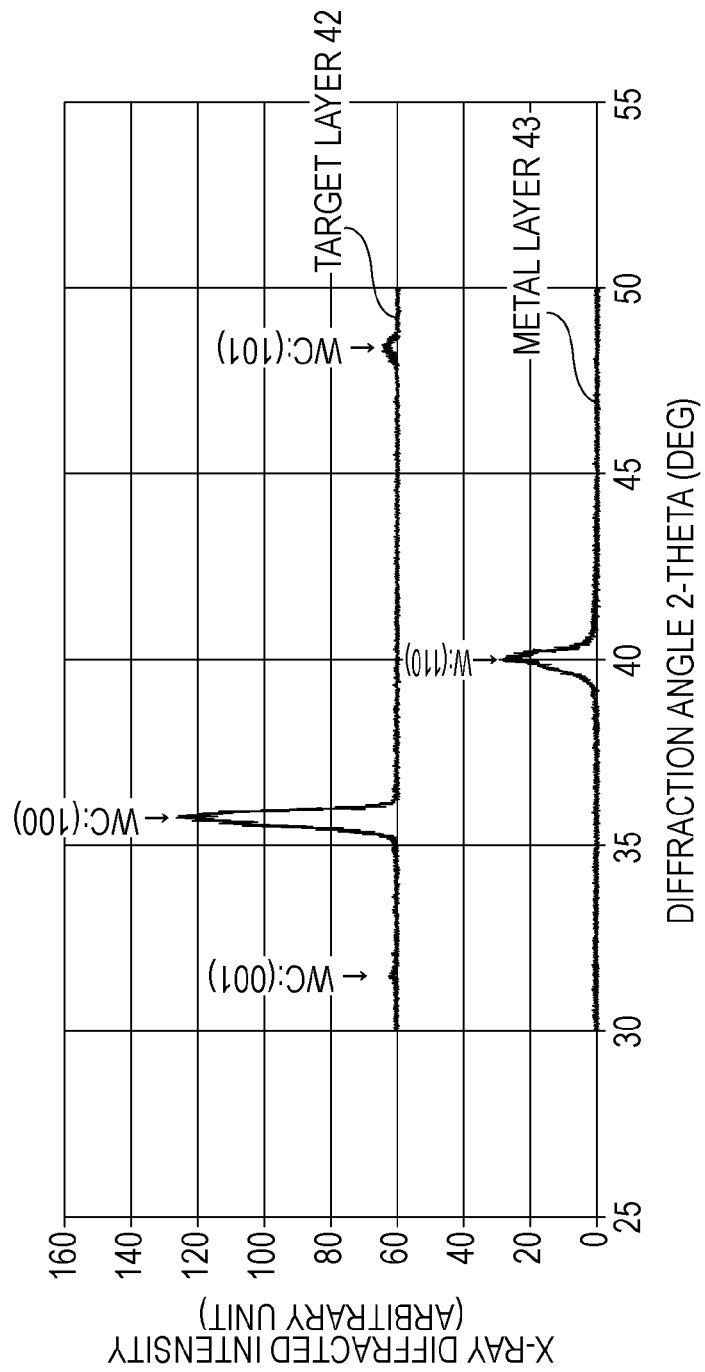
FIG. 6 shows an X-ray diffraction chart (the upper plots) of the target layer of the transmission type target described in Example 1 and an X-ray diffraction chart (the lower plots) of the metal layer of a reference example.

FIG. 5A shows a schematic view of the transmission type target 9 produced in this Example. The procedure of producing the transmission type target 9 in this example is shown in FIGS. 4B-1 to 4B-4. FIG. 6 shows the results of X-ray diffraction analysis of the target layer 42 of the transmission type target 9 of this Example and the metal layer 43 during the process of forming the transmission type target 9. The radiation generating tube 1 having the transmission type target 9 produced in this Example is shown in FIG. 2, and the radiation generator 20 having the radiation generating tube 1 is shown in FIG. 3.

First, as shown in FIG. 4B-1, a diamond base material 41 of a single-crystalline diamond having a diameter of 6 mm and a thickness of 1 mm was prepared. Subsequently, the diamond base material 41 was washed with an UV-ozone asher to remove the organic materials remaining on the surfaces. The prepared single-crystalline diamond base material contained 50 ppm of nitrogen in diamond.

Subsequently, as shown in FIG. 4B-2, a metal layer 43 having a thickness of 5 micrometers was formed on one clean surface of the diamond base material 41 by sputtering using an argon gas as the carrier gas and a tungsten sintered compact as the sputtering target.

The layer structure of the metal layer 43 prepared in this step was evaluated by X-ray diffraction analysis. A diffraction peak of (110) plane derived from pure metal tungsten was recognized at a diffraction angle 2-theta of approximately 40.2 degrees. This X-ray diffraction profile is shown in the lower part of FIG. 6.

Subsequently, as shown in FIG. 4B-3, the laminate of the tungsten layer 43 and the diamond base material 41 was placed in an image furnace of which inner pressure was reduced. Subsequently, the image furnace was heated to 1600 degrees Celsius for carbonizing the tungsten layer 43 to produce a transmission type target 9 having a target layer 42.

The layer structure of the target layer 42 prepared in this step was evaluated by X-ray diffraction analysis. A plurality of diffraction peaks derived from monotungsten carbide (WC) were recognized. Specifically, a main peak at a diffraction angle 2-theta of approximately 35.6 degrees and a sub-peak at a diffraction angle 2-theta of approximately 48.3 indicated (100) plane and (101) plane, respectively, derived from monotungsten carbide (WC). This X-ray diffraction profile is shown in the upper part of FIG. 6.

The X-rays used in the X-ray diffraction analysis were K-alpha-rays (8.05 keV) of copper (Cu), where the K-beta-rays were removed with a nickel (Ni) filter.

As shown in FIG. 6, the metal layer 43 on the diamond base material 41 before the heat treatment was identified as pure metal tungsten, and the target layer 42 on the diamond base material 41 after the heat treatment was identified as monotungsten carbide (WC). The unit of diffraction peak intensity indicated in the vertical axis of FIG. 6 is arbitrary.

Subsequently, a cross section of the resulting transmission type target 9 was subjected to mechanical polishing and FIB processing to prepare a cross-section sample 51 including the interface between the target layer 42 and the diamond base material 41. The distributions of composition and bonds in the prepared sample 51 were mapped by X-ray electron spectroscopy (XPS). It was observed that tungsten was uniformly present corresponding to the thickness of the target layer 42 and that carbon was uniformly present corresponding to the target layer 42 and the diamond base material 41. A sample S2 for observation with a transmission electron microscope (TEM) was prepared by FIB processing as in the sample 51. The crystallinity distribution, crystal orientation distribution, and composition distribution of the sample S2 were evaluated by mapping with a combination of high-resolution image observation with a transmission electron microscope, electron diffraction analysis (ED), and electron beam spectroscopy (EDX). As a result, a crystalline structure caused by hexagonal crystal monotungsten carbide corresponding to the target layer 42 was confirmed by the electron diffraction and the high-resolution image.

Subsequently, the resulting transmission type target 9 was placed in a vacuum chamber (not shown) equipped with an electron gun (not shown), and the target layer 42 was irradiated with convergent electron beams 5 emitted from the electron emission source 3. As a result, emission of characteristic X-rays derived from the K-alpha-rays of tungsten was confirmed. On this occasion, a voltage of 100 kV was applied between the electron gun and the transmission type target 9.

Figure 7:
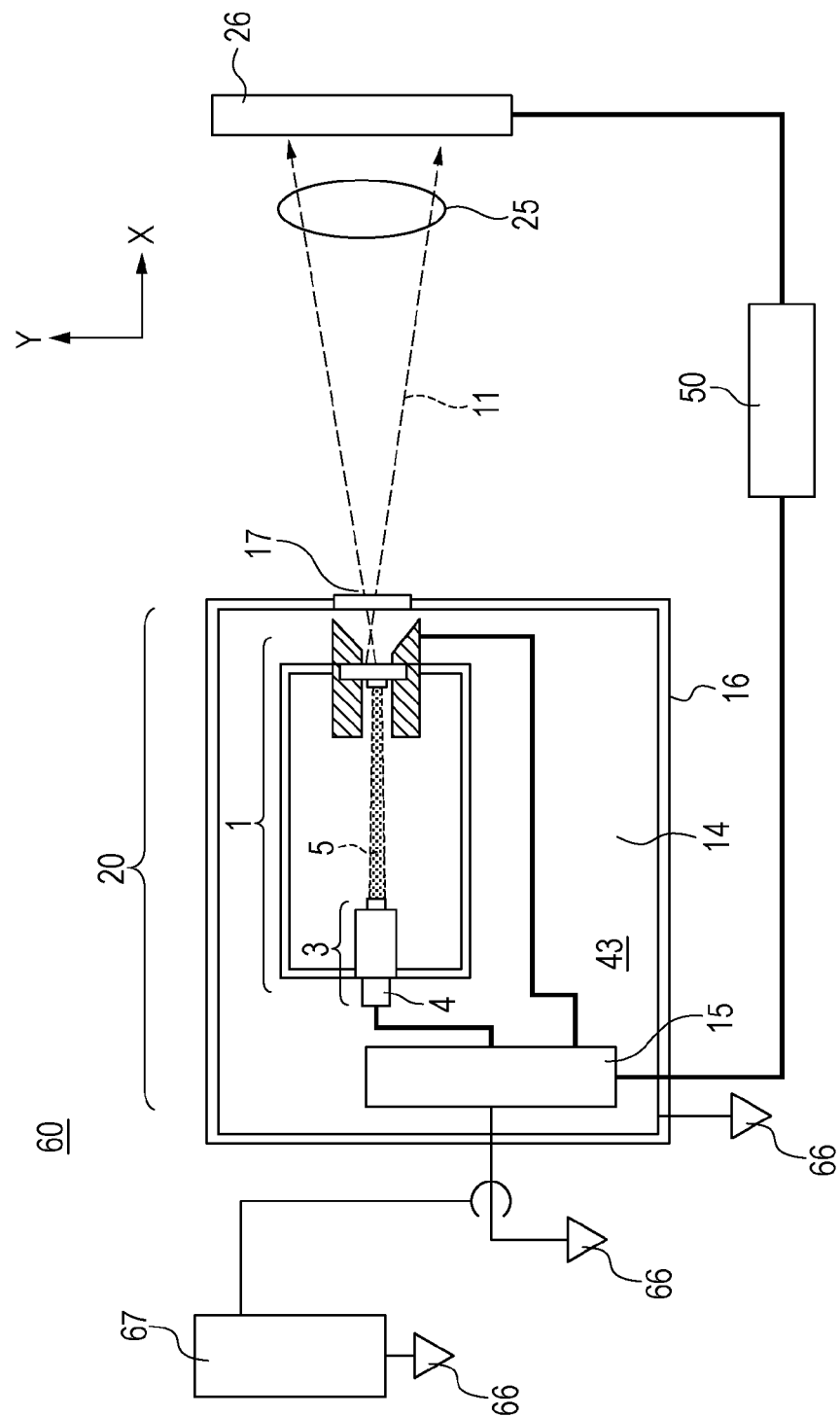
FIG. 7 is an explanatory diagram of a system for evaluating stability in radiation output of the radiation generators described in Examples 1 and 2.
Figure 8A:
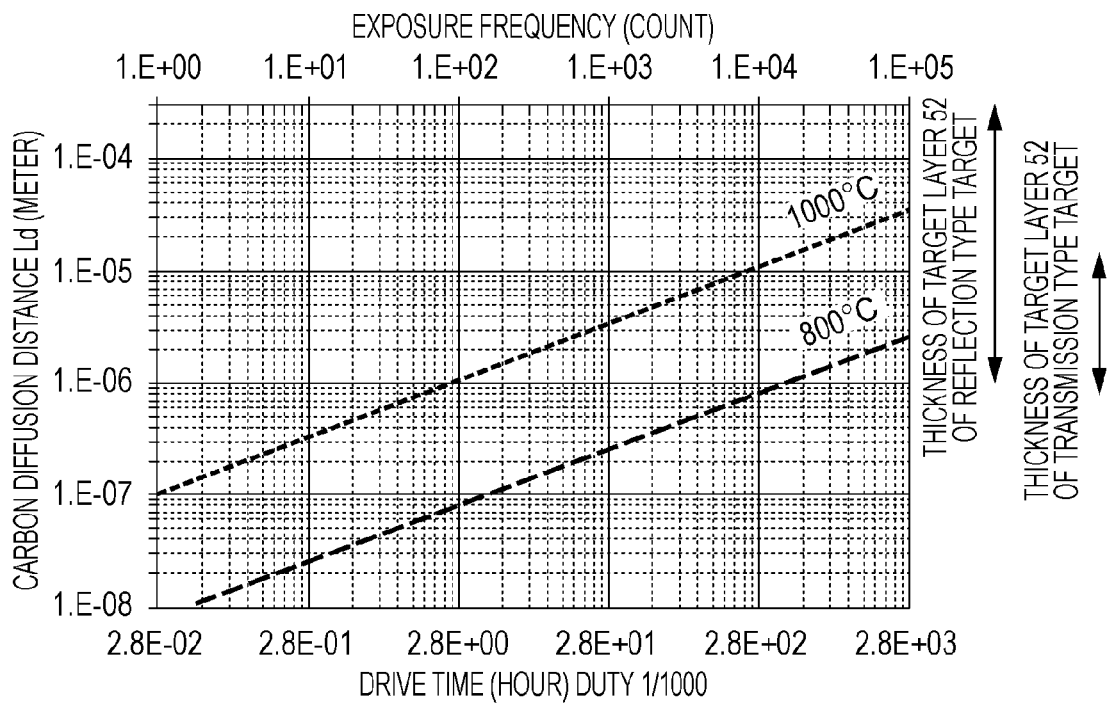
FIG. 8A is a graph showing drive time-dependency of the diffusion length of carbon in tungsten.
Figure 8B:
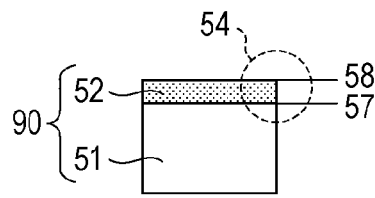
FIG. 8B is a calculation model of FIG. 8A.
Figure 8C:
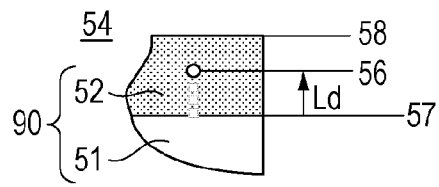
FIG. 8C is a partial enlarged view of FIG. 8B.
Figure 8D:
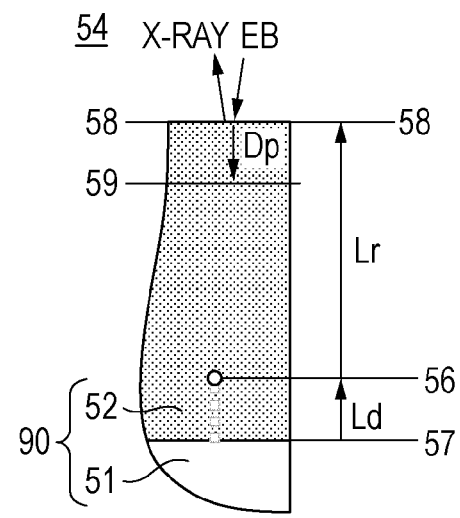
FIG. 8D is an explanatory diagram showing the influence of a carbon diffusion length in a reflection type target.
Figure 8E:
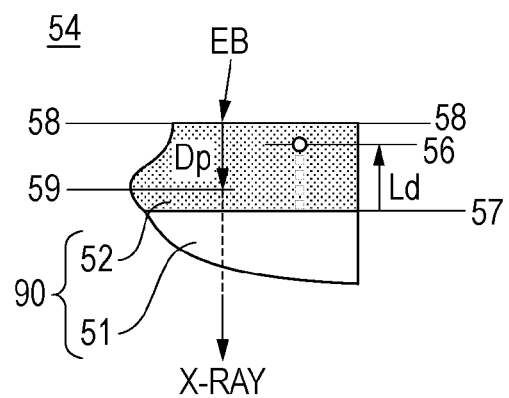
FIG. 8E is an explanatory diagram showing the influence of a carbon diffusion length in a transmission type target.

Subsequently, the transmission type target 9 produced in this Example was connected to an anode member (not shown) made of Kovar to form an anode. Subsequently, the electron emission source 3 including an impregnation type electron gun having lanthanum boride ($LaB_6$) as the electron-emitting unit 2 was connected to a cathode member (not shown) made of Kovar to form a cathode. The cathode and the anode were connected to the respective openings of an insulating tube made of aluminum with silver solder. Finally, the inside of a container surrounded by the anode, the cathode, and the insulating tube was evacuated to a vacuum state at a level of $1 \times 10^{-6}$ Pa. Thus, the radiation generating tube 1 shown in FIG. 2 was produced. Furthermore, the radiation generator 20 shown in FIG. 3 was produced using the radiation generating tube 1, and an evaluation system shown in FIG. 7 for evaluating the drive stability of the radiation generator 20 was further prepared.

The evaluation of the drive stability of the radiation generator 20 was performed by pulse drive of the electron-emitting unit 2 by alternately repeating a irradiation period of 2 seconds and a nonirradiation period of 2 seconds for 198 seconds such that an accelerating voltage of +100 kV was applied to the transmission type target 9 and that the target layer 42 was irradiated with electrons at a current density of 4 $mA/mm^2$. In the evaluation of stability of radiation output intensity, the current flowing from the target layer 42 to the earth electrode 66 was measured, and the variation in the current density of the electrons irradiated to the target layer 42 was controlled within 1% by a negative feedback circuit (not shown). Furthermore, stable driving without electric discharge during the evaluation of driving of the radiation generator 20 was confirmed with a discharge counter 67.

The stability of the radiation output intensity of the radiation generator 20 was evaluated through pulse drive of the electron emission source 3 under the above-described conditions. The driving of the radiation generator was stopped every 100 hours for 1 hour so that the temperature of the entire radiation generating tube 1 was equilibrated to room temperature, and the radiation output intensity was measured with a radiation dosimeter 26. The mean value of signal intensities detected with the radiation dosimeter 26 for 1 second was used as the radiation output intensity. The stability was evaluated by the fluctuation rate of the radiation output intensity at each elapsed time relative to the initial radiation output intensity. The results at elapsed times of 100 hours, 200 hours, and 400 hours are shown in Table 1.

TABLE 1

| | Accumulated operation time | | | |
|---|---|---|---|---|
| | 0 h (initial) | 100 h | 200 h | 400 h |
| Fluctuation rate of radiation output intensity | 1 | 0.99 | 0.97 | 0.96 |

It was demonstrated that the radiation generator 13 having the transmission type target 9 in this Example can give stable radiation output intensity even after a long time drive history.

Furthermore, after the driving test, the transmission type target 9 was taken out from the radiation generating tube 1 and was observed. No detachment between the target layer 42 and the diamond base material 41 was observed.

The density of the target layer 42 in this Example measured by RBS was $15.8 \times 10^3$ (kg/m$^3$), and the penetration depth Dp of incident electrons having a kinetic energy of 100 keV was $4.2 \times 10^{-6}$ (m). Accordingly, it was confirmed that in the radiation generating tube operated with a tube voltage of 100 kV, a metal carbide layer mainly containing monotungsten carbide was formed at least in the region from the surface of the target layer 42 to the electron penetration depth Dp.

Example 2

A transmission type target 9, a radiation generating tube 1, and a radiation generator 20 were produced as in EXAMPLE 1 except that the transmission type target 9 was produced by the method shown in FIGS. 4A-1 and 4A-2. Furthermore, the drive stability of the radiation generator 20 in EXAMPLE 2 was evaluated using the drive evaluation system in EXAMPLE 1.

In this Example, a target layer 42 having a thickness of 6 micrometers of monotungsten carbide (WC) was formed on a diamond base material 41 by CVD. FIG. 5A shows the schematic structure of the transmission type target 9 prepared in this Example.

The layer structure of the resulting target layer 42 was evaluated by X-ray diffraction analysis as in EXAMPLE 1. A plurality of diffraction peaks derived from monotungsten carbide (WC) were recognized. Specifically, a main peak at a diffraction angle 2-theta of approximately 35.6 degrees and a sub-peak at a diffraction angle 2-theta of approximately 48.3 degrees indicated (100) plane and (101) plane, respectively, derived from monotungsten carbide (WC). Cross-section samples S3 and S4 were prepared as in EXAMPLE 1. The distributions of composition and bonds in the prepared sample S3 were mapped by X-ray electron spectroscopy (XPS). Tungsten was observed corresponding to the target layer 42, and carbon was observed corresponding to the target layer 42 and the diamond base material 41. The crystallinity distribution, crystal orientation distribution, and composition distribution of the cross-section sample S4 were evaluated by mapping with a combination of high-resolution image observation with a transmission electron microscope, electron diffraction analysis (ED), and electron beam spectroscopy (EDX) as in EXAMPLE 1. The resulting crystal orientation distribution was mapped. As a result, a crystalline structure caused by hexagonal crystal monotungsten carbide corresponding to the target layer 42 was confirmed by the electron diffraction and the high-resolution image.

The density of the target layer in this Example measured by RBS was $15.9 \times 10^3$ (kg/m$^3$), and the penetration depth Dp of incident electrons having a kinetic energy of 100 keV was $4.2 \times 10^{-6}$ (m). Accordingly, it was confirmed that in the radiation generating tube 1 operated with a tube voltage of 100 kV, a metal carbide layer mainly containing monotungsten carbide was formed at least in the region from the surface of the target layer 42 to the electron penetration depth Dp.

The stability of the radiation output intensity of the radiation generator 20 was evaluated as in EXAMPLE 1. The results are shown in Table 2.

TABLE 2

| | Accumulated operation time | | | |
|---|---|---|---|---|
| | 0 h (initial) | 100 h | 200 h | 400 h |
| Fluctuation rate of radiation output intensity | 1 | 0.99 | 0.98 | 0.97 |

It was demonstrated that the radiation generator 13 having the transmission type target 9 in this Example can give stable radiation output intensity even after a long time drive history.

Furthermore, after the driving test, the transmission type target 9 was taken out from the radiation generating tube 1 and was observed. No detachment between the target layer 42 and the diamond base material 41 was observed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-251083, filed Nov. 15, 2012, which is hereby incorporated by reference herein in its entirety.

The invention claimed is:

1. A transmission type target comprising:
    a target layer generating an X-ray with an electron irradiation; and
    a support member contains carbon and supports the target layer,
    wherein the target layer contains carbon as a metal carbide.

2. The transmission type target according to claim 1, wherein the target layer contains a target metal generating an X-ray with an electron irradiation.

3. The transmission type target according to claim 2, wherein the target metal contains at least one metal selected from a group consisting of molybdenum, tantalum, and tungsten.

4. The transmission type target according to claim 1, wherein the metal carbide is located as a metal carbide layer on the support member.

5. The transmission type target according to claim 1, wherein the metal carbide is distributed along a thickness direction of the target layer.

6. The transmission type target according to claim 1, wherein the metal carbide is located in a region at where an X-ray is generated.

7. The transmission type target according to claim 1, wherein the metal carbide is uniformly distributed in a thickness direction of the target layer.

8. The transmission type target according to claim 1, wherein the target layer is a metal carbide layer constituted of the metal carbide.

9. The transmission type target according to claim 1, wherein the target layer contains ditungsten carbide and monotungsten carbide such that the atomic concentration of the ditungsten carbide is less than that of the monotungsten carbide.

10. The transmission type target according to claim 1, wherein the target layer contains dimolybdenum carbide and monomolybdenum carbide such that the atomic concentration of the dimolybdenum carbide is higher than that of monomolybdenum carbide.

11. The transmission type target according to claim 1, wherein the target layer contains ditantalum carbide and monotantalum carbide such that the atomic concentration of the ditantalum carbide is less than that of monotantalum carbide.

12. The transmission type target according to claim 1, wherein the target layer contains at least one of hexagonal crystal dimolybdenum carbide, cubic crystal monotantalum carbide, and hexagonal crystal monotungsten carbide.

13. The transmission type target according to claim 1, wherein the peripheral edge of the target layer is separated from the peripheral edge of the base material; the transmission type target has an electrode bridging the peripheral edge of the target layer and the peripheral edge of the base material; and the electrode is constituted of a carbide of a metal different from the metal contained in the target layer.

14. The transmission type target according to claim 1, wherein the support member is a diamond base material.

15. The transmission type target according to claim 14, wherein the diamond base material is polycrystalline diamond.

16. The transmission type target according to claim 1, wherein the target layer is directly supported by the support member.

17. An X-ray generating tube comprising:
the transmission type target according to claim 1;
an electron emission source having an electron-emitting unit facing the target layer with a distance therebetween; and
an envelope at least containing the electron-emitting unit and the target layer in the interior space or on the inner surfaces thereof.

18. An X-ray generating apparatus comprising:
the X-ray generating tube according to claim 17; and
a drive circuit that is electrically connected to both the target layer and the electron-emitting unit and outputs a tube voltage to be applied between the target layer and the electron-emitting unit.

19. The X-ray generating apparatus according to claim 18, wherein the metal carbide is located in a region along a thickness direction of the target layer from a surface received electrons to an electron penetration depth Dp (m) defined by a following Expression 1:

$$Dp = 6.67 \times 10^{-10} \times Va^{1.6}/rho \quad \text{[Expression 1]}$$

wherein Va represents the tube voltage (V), and rho represents the density (kg/m$^3$) of the target layer.

20. An X-ray imaging system comprising:
the X-ray generating apparatus according to claim 18 and
an X-ray detector detecting an X-ray emitted from the radiation generator and permeated through a subject.

21. A target for an X-ray generating tube comprising:
a target layer generating an X-ray with an electron irradiation; and
a support member containing carbon and supporting the target layer,
wherein the target layer contains carbon as a metal carbide located in a region at where an X-ray is generated.

22. The target according to claim 21, wherein the target layer contains a target metal generating an X-ray with an electron irradiation.

23. The target according to claim 22, wherein the target metal contains at least one metal selected from a group consisting of molybdenum, tantalum, and tungsten.

24. The target according to claim 21, wherein the metal carbide is located as a metal carbide layer on the support member.

25. The target according to claim 21, wherein the metal carbide is distributed along a thickness direction of the target layer.

26. An X-ray generating tube comprising:
the target according to claim 21;
an electron emission source having an electron-emitting unit facing the target layer with a distance therebetween; and
an envelope at least containing the electron-emitting unit and the target layer in the interior space or on the inner surfaces thereof.

27. An X-ray generating apparatus comprising:
the X-ray generating tube according to claim 26; and
a drive circuit that is electrically connected to both the target layer and the electron-emitting unit and outputs a tube voltage to be applied between the target layer and the electron-emitting unit.

28. The X-ray generating apparatus according to claim 27, wherein the metal carbide is located in a region along a thickness direction of the target layer from a surface received electrons to an electron penetration depth Dp (m) defined by a following Expression 1:

$$Dp = 6.67 \times 10^{-10} \times Va^{1.6}/rho \quad \text{[Expression 1]}$$

wherein Va represents a tube voltage (V), and rho represents a density (kg/m$^3$) of the target layer.

29. An X-ray imaging system comprising:
the X-ray generating apparatus according to claim 27; and
an X-ray detector detecting an X-ray emitted from the X-ray generating apparatus and permeated through a subject.

30. A method of producing a transmission type target having a target layer including a metal carbide, the method comprising:
preparing a diamond base material;
forming a metal layer comprising at least one metal selected from molybdenum, tantalum, and tungsten on one surface of the diamond base material; and
forming a metal carbide layer containing a carbide of the metal by heating the diamond base material provided with the metal layer to diffuse carbon from the diamond base material to the metal layer and to cause carbonization.

31. The method of producing a transmission type target according to claim 30, wherein the formation of the metal carbide layer is performed under an inert gas atmosphere or a reduced-pressure atmosphere at a temperature of 1000 degrees Celsius or more and 2000 degrees Celsius or less.

32. The method of producing a transmission type target according to claim 30, wherein the preparation of the diamond base material is formation of polycrystalline diamond by chemical vapor deposition.

* * * * *